(12) United States Patent
Kennedy, II et al.

(10) Patent No.: US 7,976,496 B2
(45) Date of Patent: Jul. 12, 2011

(54) BALLOON FOLDING CONTROL MECHANISM

(75) Inventors: Kenneth C. Kennedy, II, Clemmons, NC (US); Matthew P. Carter, Dobson, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 284 days.

(21) Appl. No.: 12/168,450

(22) Filed: Jul. 7, 2008

(65) Prior Publication Data
US 2009/0024087 A1 Jan. 22, 2009

Related U.S. Application Data

(60) Provisional application No. 60/958,849, filed on Jul. 9, 2007.

(51) Int. Cl.
*A61M 29/00* (2006.01)
(52) U.S. Cl. .................................. 604/99.01; 604/96.01
(58) Field of Classification Search .... 604/96.01–97.01, 604/98.01, 99.01, 103, 103.09
See application file for complete search history.

(56) References Cited

U.S. PATENT DOCUMENTS

| | | | | |
|---|---|---|---|---|
| 4,813,934 A * | 3/1989 | Engelson et al. | ........... | 604/99.02 |
| 5,209,727 A * | 5/1993 | Radisch et al. | ............ | 604/96.01 |
| 5,279,560 A | 1/1994 | Morrill et al. | | |
| 5,318,587 A | 6/1994 | Davey | | |
| 5,423,755 A | 6/1995 | Kesten et al. | | |
| 5,454,788 A * | 10/1995 | Walker et al. | .............. | 604/99.04 |
| 6,033,381 A * | 3/2000 | Kontos | ..................... | 604/164.13 |
| 6,425,882 B1 | 7/2002 | Vigil | | |
| 6,428,568 B2 * | 8/2002 | Gaudoin et al. | ............. | 623/1.11 |
| 6,517,514 B1 | 2/2003 | Campbell | | |
| 2003/0158516 A1 | 8/2003 | Wholey et al. | | |
| 2008/0171977 A1 * | 7/2008 | Blix | ........................... | 604/96.01 |
| 2008/0306441 A1 * | 12/2008 | Brown et al. | ............. | 604/99.01 |
| 2010/0217185 A1 * | 8/2010 | Terliuc et al. | ............. | 604/96.01 |

FOREIGN PATENT DOCUMENTS

| | | |
|---|---|---|
| EP | 0724891 A1 | 8/1996 |
| EP | 1120129 A1 | 8/2001 |
| GB | 2046096 A | 11/1980 |
| JP | 2001-238953 | 9/2001 |
| WO | WO 93/18816 | 9/1993 |
| WO | WO 2004/101059 A1 | 11/2004 |

* cited by examiner

*Primary Examiner* — Nicholas D Lucchesi
*Assistant Examiner* — Gerald Landry, II
(74) *Attorney, Agent, or Firm* — Brinks Hofer Gilson & Lione

(57) ABSTRACT

A balloon catheter including an inflatable balloon affixed to a catheter. The proximal end of the balloon is affixed to the distal end of the catheter so as to provide an air tight seal there between. A stiffening member extends distally of the distal end of the catheter and forms a slip joint connection with the distal end of the balloon to permit the distal end of the balloon to axially move or translate relative to the distal end of the catheter. The slip joint allows the axial length of balloon to change during inflation or deflation without transferring tensile or compressive forces between the balloon and the catheter. A balloon folding control mechanism is disposed about the portion of the stiffening member traversing the interior of the balloon, and is configured to promote refolding of the balloon into a predetermined and desired folding configuration upon deflation.

29 Claims, 13 Drawing Sheets

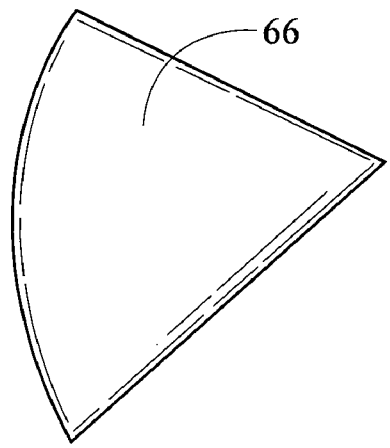 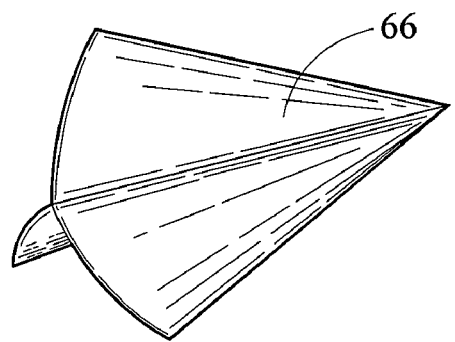
Fig. 10        Fig. 11
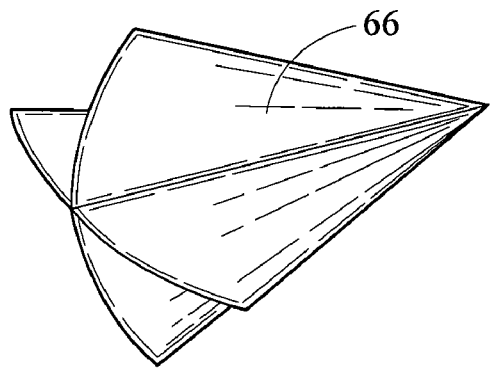 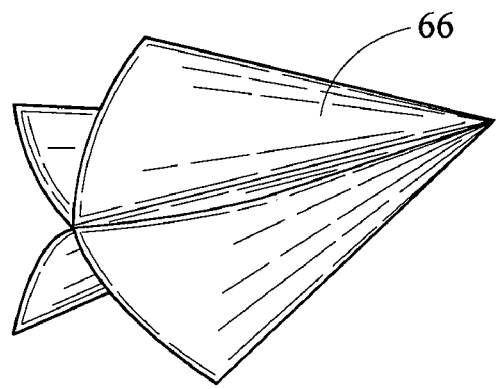
Fig. 12        Fig. 13

BALLOON FOLDING CONTROL MECHANISM

CROSS-REFERENCE TO RELATED APPLICATIONS

This application claims the benefit of U.S. Provisional Application Ser. No. 60/958,849, filed Jul. 9, 2007, entitled "Balloon Folding Control Mechanism", the entire contents of which are incorporated by reference.

TECHNICAL FIELD

This invention relates to medical devices, and more particularly to balloon catheters that can be placed within a body lumen and inflated to perform various medical procedures. The invention is especially relevant to balloon catheters with balloons formed of non-elastomeric (semi-rigid) films or materials, wherein the film that forms the balloon is folded and unfolded during deflation and inflation, respectively, of the balloon.

BACKGROUND OF THE INVENTION

Balloon catheters are used to perform various medical procedures wherein the balloon is positioned within a body lumen or canal and subsequently inflated. In some of these medical procedures, such as in an angioplasty procedure, the balloon is inflated so as to expand the interior volume of the body canal. In this type of procedure, the balloon is expanded to apply pressure to the interior surface of the body canal to thereby compress any tissue protruding into the canal and thereby enlarge the interior volume thereof. Once the tissue has been compressed, and the body canal widened, the balloon is deflated and removed.

In other types of medical procedures, such as photodynamic therapy (PDT), a balloon catheter is used to align and stabilize the catheter within the body lumen. For example, the balloon catheter may be inflated under low pressure within a body lumen such as the esophagus. A therapeutic fiber optic device is then inserted into the catheter in the vicinity of the balloon. The therapeutic fiber optic device is then used to emit light waves to treat the surrounding tissue. In this procedure, the balloon is used to both align the catheter in the center of the body lumen, and to prevent the catheter from moving during the PDT procedure. However, the tissue to be treated must not be unduly compressed by the expanded balloon. Thus, the balloon is expanded only enough to lightly contact the interior surface of the lumen and align the catheter.

As will be explained below, conventional balloon catheters have a number of shortcomings that make them inadequate for many of the above-described procedures, and in particular, for PDT procedures.

A typical balloon catheter 10 is shown in FIGS. 1A-1D. As best seen in FIG. 1A, a conventional balloon catheter 10 comprises a balloon 12 that is affixed to a catheter 14. The balloon 12 is typically manufactured from a non-elastomeric material (e.g., a semi-rigid or non-compliant material), and includes a distal neck or end 16, a proximal neck or end 18 and a central portion 20. The balloon 12 is affixed to the catheter 14 by inserting the distal end 22 of the catheter 14 into and through the proximal end 18 of the balloon 12. The balloon 12 is then slid over the catheter 14 until the distal end 22 of the catheter 14 is inserted into the distal end 16 of the balloon 12. The distal end 22 of the catheter 14 is then affixed to the distal end 16 of the balloon 12 by an adhesive, ultrasonic welding, or some other method. The proximal end 18 of the balloon 12 is similarly affixed to the outer wall of the catheter 14 so as to anchor and seal the proximal end of the balloon 12.

The catheter 14 includes an aperture 24 for the introduction of air or some other fluid into the interior volume of the balloon 12. Although not shown in the drawings, the proximal end of the catheter 14 is typically attached to a device, such as a syringe, that is manipulated to either inflate or deflate the balloon 12 by injecting a fluid into or withdrawing a fluid from, respectively, the interior volume of the balloon 12.

The conventional balloon catheter 10 has a number of drawbacks for use in many of the above-described procedures, and in particular, for use in PDT procedures. When initially manufactured, the balloon catheter 10 generally assumes a shape and configuration as depicted in FIG. 1A. As can be seen in this drawing, the central portion 20 of the balloon 12 is connected to the distal end 16 and the proximal end 18 by tapered or conical sections 26. The tapered sections 26 provide a transition between the larger diameter of the central portion 20 of the balloon 12 and the smaller end portions of the balloon 12 (i.e., the distal end 16 and the proximal end 18) that are connected to the catheter 14.

At the time of packaging by the manufacturer or at the initiation of the medical procedure, the balloon 12 is typically deflated prior to inserting of the balloon catheter 10 into the body canal. Deflation of the balloon 12 is necessary to reduce the overall cross-section or diameter of the device to permit it to pass through an endoscope and/or to navigate and pass through the body's internal canals. FIG. 1B depicts the balloon catheter 10 in the deflated state. As can be seen in this drawing, the balloon 12 is forced to compress in length. This is because the overall length of the material that forms the central portion 20 and the tapered portions 26, as measured along the surface of the balloon 12 in a generally axial direction of the catheter 14 (i.e., from one end of the balloon 12 to the other), is greater than the distance between the distal end 16 and the proximal end 18. As a result of this compression, transverse creases 28 typically form along the surface of the balloon 12.

After the balloon catheter 10 is positioned within the body canal (not shown) at the desired location, inflation of the balloon 12 is initiated as shown in FIG. 1C. As depicted in this drawing, the creases 28 in the surface of the material may prevent the balloon 12 from fully expanding to its normal length (i.e., as shown in FIG. 1A). In other words, the balloon 12 tends to act like a spring under tension. As a result, the portion of the catheter 14 that lies between the distal end 16 and the proximal end 18 of the balloon 12 will be forced into compression, and may begin to bow 30 as a result of these compressive forces.

As inflation of the balloon 12 continues, bowing 30 of the catheter 14 may be increased as shown in FIG. 1D. This is the result of transverse or outward expansion of the central portion 20 of the balloon, which tends to pull the distal end 16 and the proximal end 18 towards each other.

Bowing 30 of the catheter 14 may not be eliminated unless and until a sufficiently high inflation pressure is applied to the balloon 12 (see FIG. 1A). However, some bowing 30 of the catheter 14 may nevertheless remain if the initial deflation of the balloon 12 (see FIG. 1B) resulted in the formation of permanent transverse creases 28. Permanent bowing 30 of the catheter 14 is more likely if the balloon 12 is constructed from a non-elastomeric material.

The formation of transverse creases 28 and the bowing 30 of the catheter 14 can negatively impact the use of the conventional balloon catheter 10 during certain medical procedures. For example, during angioplasty procedures, permanent creases 28 in the surface of the balloon 12 may prevent the complete or uniform compression of the tissue on the interior surface of the body canal against which the balloon 12 is expanded. This may result in a decrease in effectiveness of the angioplasty procedure.

With respect to PDT procedures, any bowing 30 of the catheter 14 can prevent accurate alignment and centering of the catheter 14 within the body lumen or canal to be treated. This is because typical PDT procedures do not allow the expanded balloon 12 to exert excess pressure or heavy contact on the interior surface of the body lumen. Thus, the balloon 12 cannot be inflated with a pressure that is sufficient to eliminate any bowing 30 of the catheter 14. The catheter 14 may consequently not be properly centered in the body lumen. As a result, effective treatment of the body lumen tissue with the therapeutic fiber optic device, which is positioned inside the catheter 14, may be inhibited.

In addition, because the distal end 16 and the proximal end 18 of the balloon 12 are both fixed to the catheter 14 at permanent (i.e., non-moveable) locations, the ability to reduce the diameter of the deflated balloon 12 may be limited, particularly if the balloon 12 is manufactured from a non-elastomeric material. In other words, the central portion 20 of the balloon 12 may not compress tightly about the catheter 14 during deflation because of the creases 28 formed in the material of the balloon 12 (see FIG. 1B). Bunching of the balloon material may likewise limit the deflated diameter or cross-section of the balloon 12. Consequently, the device may be more difficult to maneuver during ingress or egress of the device through the body's canals. In addition, the resulting "wrinkled" surface of the balloon 12 may cause irritation to body canal tissue during ingress or egress of the device and/or prevent the device from passing through the endoscope channel.

To overcome one or more of the above-described problems and disadvantages of conventional balloon catheters, an improved balloon catheter has been developed that includes a balloon that is fixedly connected to the catheter at only a single location. An example of the improved balloon catheter 40 is shown in FIG. 2, which illustrates the distal portion of the improved balloon catheter. The balloon catheter 40 includes a rounded or cylindrically shaped balloon 42 that is affixed to a catheter 44. In particular, the proximal end 46 of the balloon 42 is fixedly connected to the distal end 48 of the catheter 44. A tapered stiffening member 50 extends distally from the distal end 48 of the catheter 44 and through the interior of the balloon 42. The distal end 52 of the stiffening member 50 forms a slip joint connection 54 with the distal end 56 of the balloon 42. The slip joint 54 allows the distal end 56 of the balloon 42 to axially move or translate with respect to the distal end 48 of the catheter 44 while maintaining axial alignment of the balloon 42 relative to the stiffening member.

The slip joint 54 allows the overall length of the balloon 42 to change during inflation or deflation. In addition, the slip joint 54 prevents the relative axial rigidity of the catheter 44 and stiffening member 50 from generating any axial tensile or compressive forces in the balloon 42. Consequently, transverse creasing of the central portion of the balloon 42 is eliminated or at least minimized. The slip joint 54 similarly prevents the balloon 42 from generating any adverse forces in the catheter 44 or stiffening member 50 during inflation or deflation of the device. Thus, the catheter 44 and stiffening member 50 will not be bowed or stretched as result of the inflation or deflation of the balloon 42. Moreover, the central portion of the balloon 42 can generally be collapsed into a smaller diameter or cross-section for ingress or egress of the balloon catheter 40 through the body's canals and/or the endoscope channel.

Although slip joint balloon catheters have overcome many of the disadvantages of conventional fixed length balloon catheters, slip joint balloon catheters may be difficult to refold into the pre-inflated folded state. For example, many semi-rigid balloon catheters are initially folded to have three or more "wings" so as to minimize the cross-sectional area and transverse creasing of the deflated balloon for delivery to the target site within the patient. After the balloon has been inflated (e.g., to perform the medical procedure), the balloon must then be deflated so that it can be removed from the patient. However, the balloon, and particularly a slip joint balloon, may not refold into the initial folded configuration. For example, the balloon may only fold into a 2-wing configuration, or may bunch up in response to the negative pressure used to deflate the balloon. This is most likely due to elongation and/or plastic deformation of the balloon during inflation. As a result, the balloon may not deflate back into the same cross-sectional area as that of the initially folded balloon. This may make it difficult or impossible to remove the balloon from the patient, particularly if the balloon catheter was introduced into the patient through an endoscope or other elongate introducer. The balloon may also get jammed in the endoscope upon withdrawal. These problems can be exacerbated with semi-rigid stageable balloons that are designed to undergo plastic deformation (permanent stretching) during inflation in order to achieve various discrete diameters at specified corresponding pressures. This is most likely due to the loss of "fold memory" in the balloon material as a result of the plastic deformation incurred by the inflation of the balloon.

What is needed is an improved slip joint balloon catheter that overcomes the disadvantages of conventional devices. In particular, what is needed is a slip joint balloon catheter that can be deflated to a minimal diameter for ingress and egress through the body's canals and/or an endoscope channel, that resists the formation of transverse creases in the surface of the balloon during deflation, and that assumes a predetermined and desired folding configuration upon deflation.

SUMMARY OF THE INVENTION

The foregoing problems are solved and a technical advance is achieved by the slip joint balloon catheter of the present invention. The balloon catheter includes a rounded or cylindrically shaped balloon that is affixed to a catheter. The balloon includes a distal end, a proximal end and a central portion, and is formed of a non-elastomeric or semi-rigid material. The proximal end of the balloon is fixedly attached to the distal end of the catheter, which terminates at or near the proximal end of the balloon. A stiffening member is disposed within the catheter and extends distally from the distal end of the catheter and traverse the interior of the balloon. The distal end of the stiffening member forms a slip joint connection with the distal end of the balloon.

The slip joint connection allows the distal end of the balloon to axially move or translate with respect to the distal end of the catheter while maintaining axial alignment of the balloon relative to the stiffening member. This prevents the relative axial rigidity of the catheter and stiffening member from generating any axial tensile or compressive forces in the balloon. Consequently, transverse creasing of the central portion of the balloon is eliminated or at least minimized. The slip joint connection similarly prevents the balloon from generating any adverse forces in the catheter or stiffening member during inflation or deflation of the device. Thus, the catheter and stiffening member will not be bowed or stretched as result of the inflation or deflation of the balloon.

The slip joint balloon catheter of the present invention further includes a balloon folding control mechanism that is configured to promote refolding of the balloon into a predetermined and desired folding configuration upon deflation. In particular, the balloon folding control mechanism is configured to promote refolding of the balloon into at least a 3-wing configuration, thereby allowing the deflated balloon to assume a minimal cross-sectional area.

In a first aspect of the invention, the balloon folding control mechanism comprises a stop member that is configured to limit shortening of the balloon to a predetermined amount. In one embodiment, the stop member is attached to the stiffening member and is configured to limit proximal movement of the distal end of the balloon relative to the stiffening member.

In a second aspect of the invention, the balloon folding control mechanism comprises a biasing member for applying a biasing force to the balloon, the biasing force being configured to inhibit shortening of the balloon and/or promote lengthening of the balloon by a predetermined amount. In one embodiment, the biasing member is spring disposed between the stiffening member and the distal end of the balloon.

These and other advantages, as well as the invention itself, will become apparent in the details of construction and operation as more fully described below. Moreover, it should be appreciated that several aspects of the invention can be used with other types of balloon catheters or medical devices.

BRIEF DESCRIPTION OF THE DRAWING

Embodiments of the present invention will now be described by way of example with reference to the accompanying drawings, in which:

FIG. 10 is an oblique view of the conical balloon element folded into a 2-wing configuration;

FIG. 11 is an oblique view of the conical balloon element folded into a 3-wing configuration;

FIG. 12 is an oblique view of the conical balloon element folded into a 4-wing configuration;

FIG. 13 is an oblique view of the conical balloon element folded into a 5-wing configuration;

DETAILED DESCRIPTION

Figure 1A:
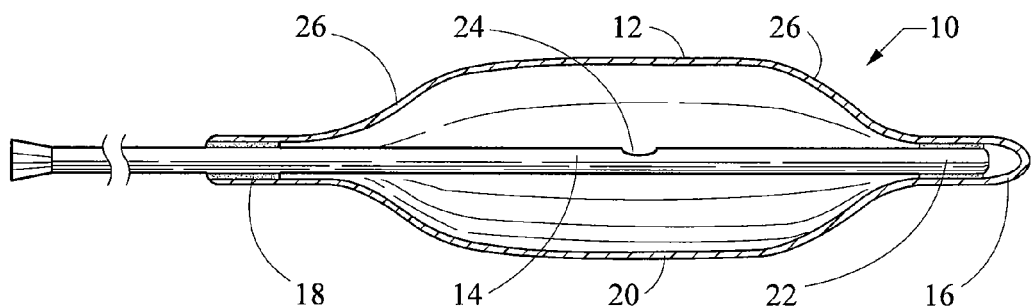
FIGS. 1A-1D depict cross-sectional side views of a conventional fixed length balloon catheter in various stages of inflation and deflation.
Figure 1B:
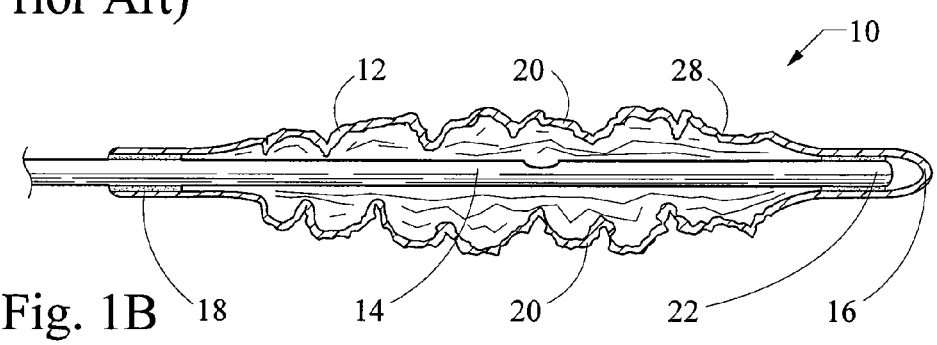
Figure 1C:
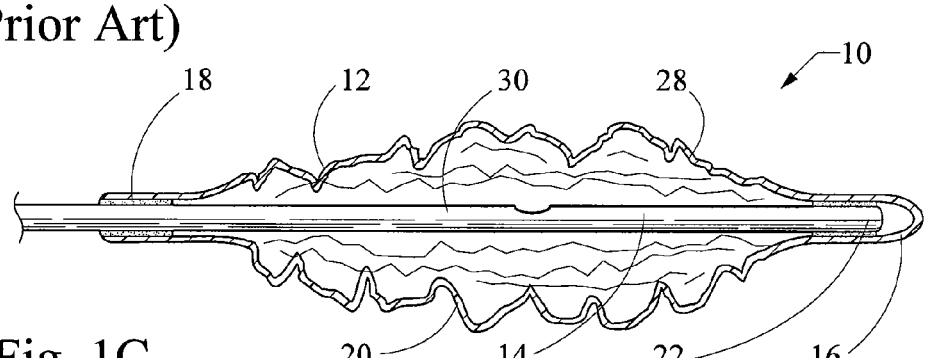
Figure 1D:
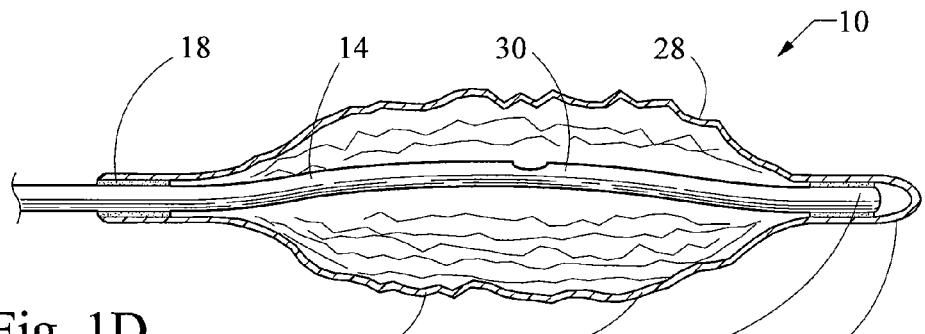
Figure 2:
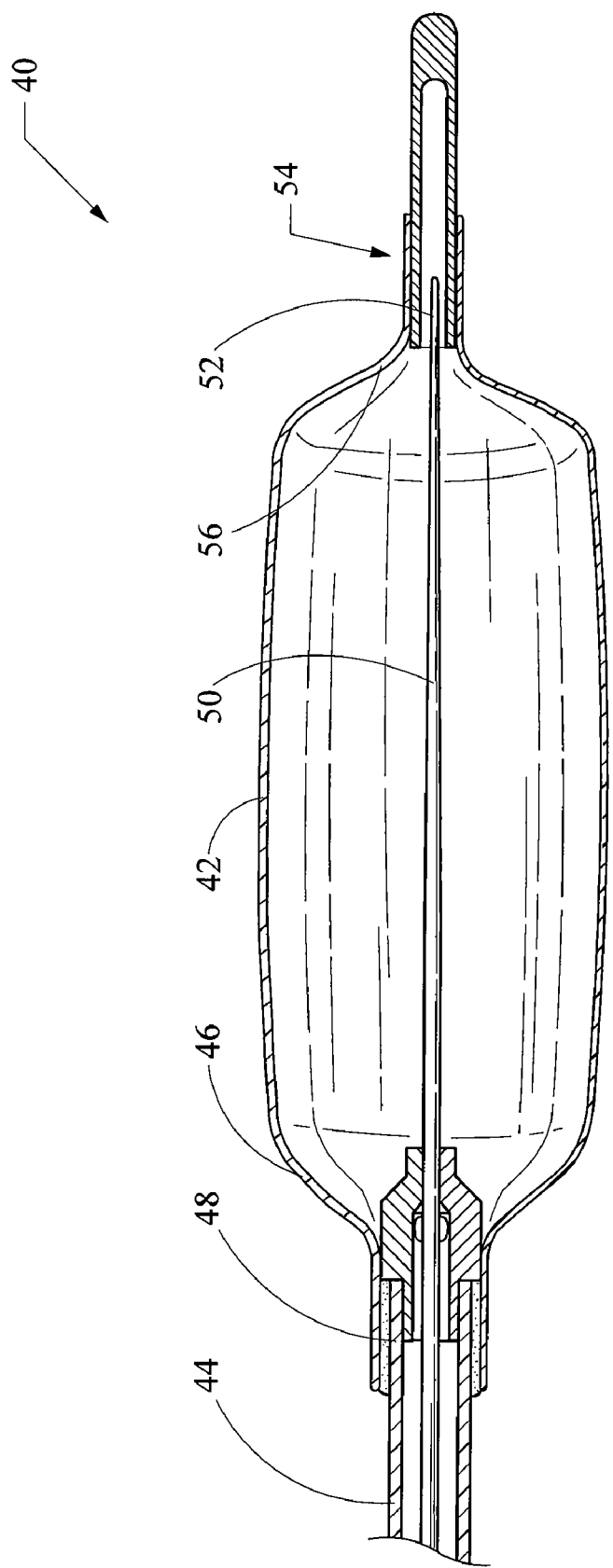
FIG. 2 depicts a cross-sectional side view of the distal portion of an exemplary slip joint balloon catheter.
Figure 3:
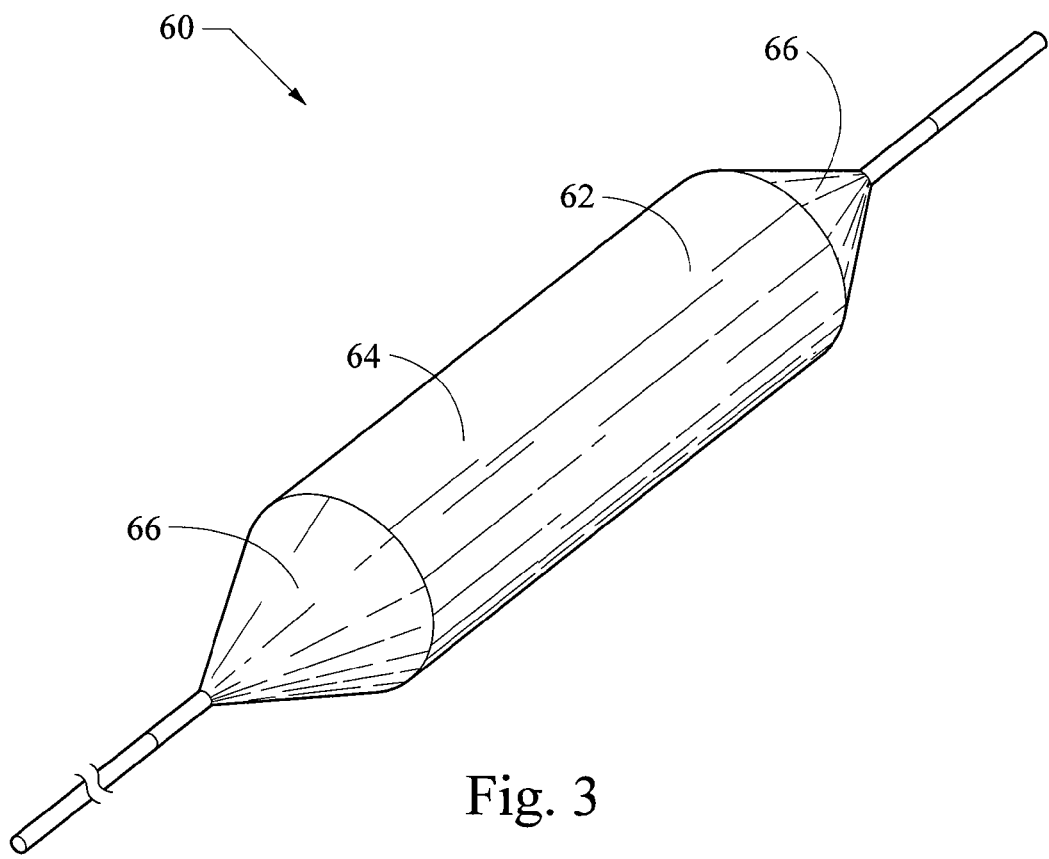
FIG. 3 is an schematic illustration of the distal portion of a conventional balloon catheter.
Figure 4:
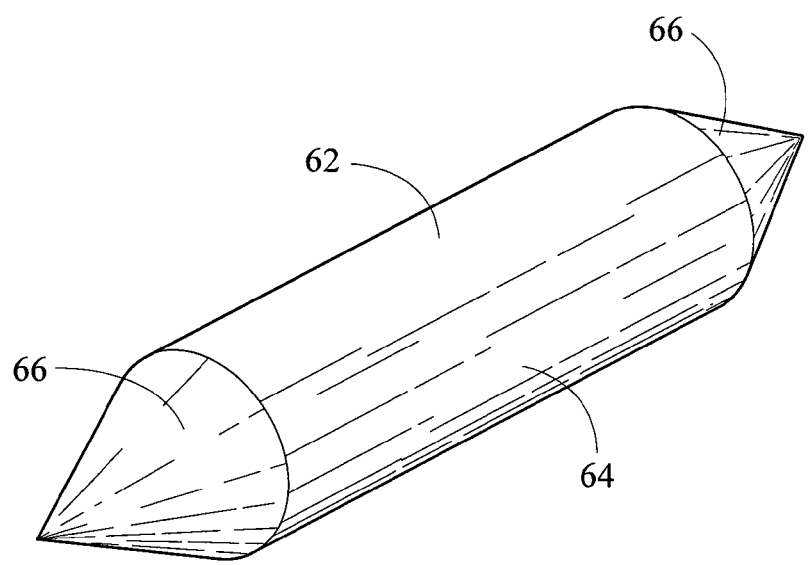
FIG. 4 is an oblique idealized view of the balloon of FIG. 3.
Figure 5:
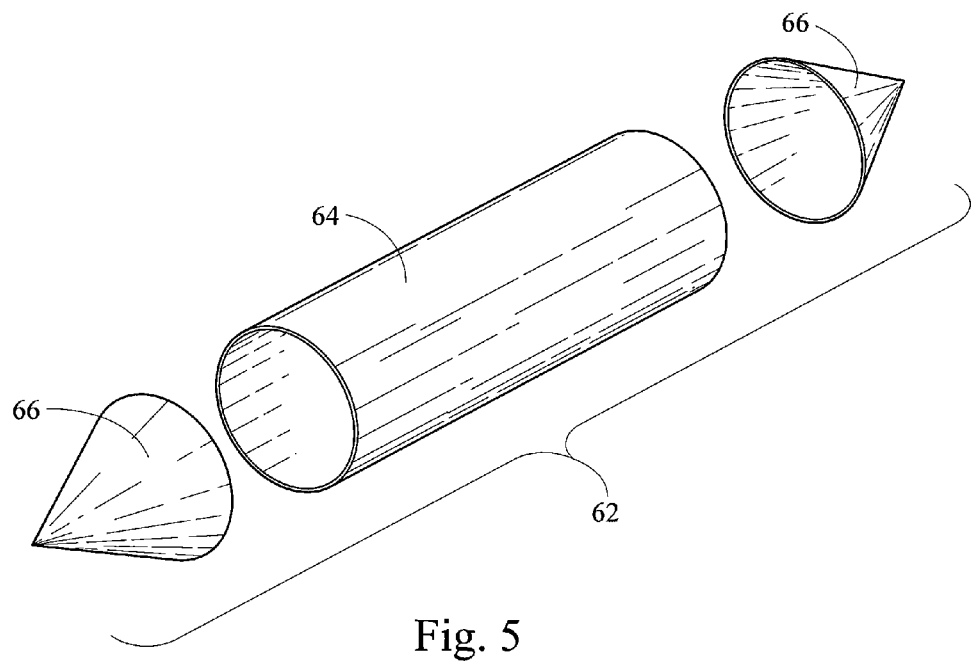
FIG. 5 is an oblique exploded view of the balloon of FIG. 4 showing the basic cylindrical and conical balloon elements.
Figure 6:
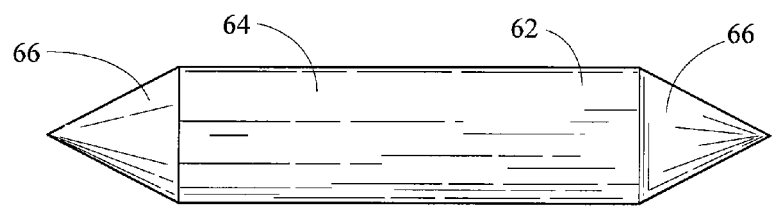
FIG. 6 is a side view of the balloon of FIG. 4.

As an initial matter, an analysis of typical balloon geometry and the folding of semi-rigid balloons will be provided in connection with FIGS. 3-18. FIG. 3 illustrates the distal portion of a medical balloon catheter 60 in which the inflated thin-wall balloon 62 generally comprises a central cylindrical central element 64 and a pair of conical end elements 66. This is the form in which the balloon 62 is typically manufactured, i.e., in the shape of the inflated state. In FIG. 4, the catheter has been removed and the inflated balloon 62 is shown in an idealized geometric form consisting of a cylindrical surface element 64 bounded by two conical surface elements 66. FIG. 5 is an exploded view of the idealized balloon 62 of FIG. 4. This geometry is further illustrated in FIGS. 6 and 7, in which the projected shapes of the cylinder element 64 and the two conical elements 66 are shown as a rectangle and a pair of triangles, respectively. As will be explained in greater detail below, the folding behavior of these forms is the subject of this analysis and will be used to illustrate certain aspects of the present invention.

Figure 7:
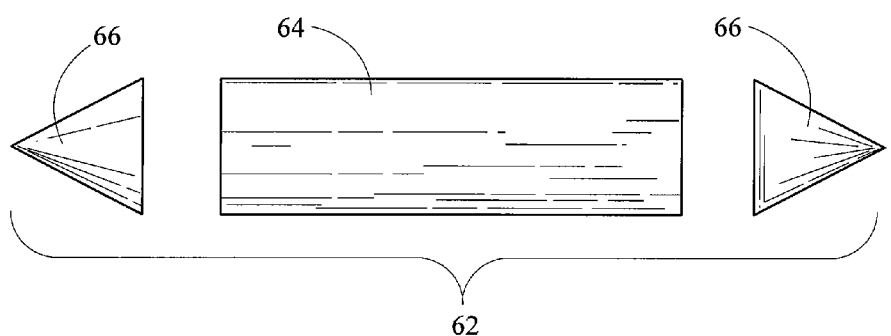
FIG. 7 is a side view of the exploded balloon of FIG. 5.
Figure 8:
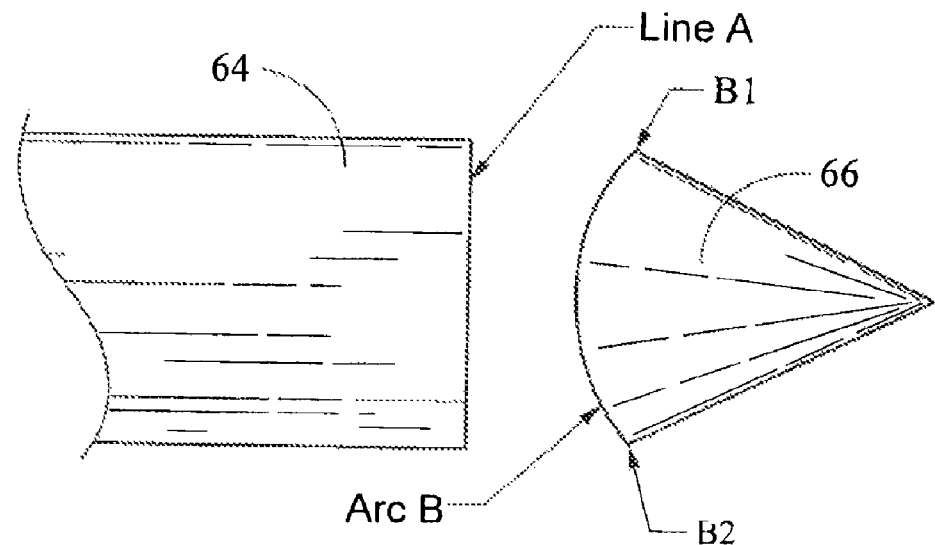
FIG. 8 is a partial side view of the exploded balloon of FIG. 5 wherein the cylindrical and conical balloon elements have been flattened into a 2-dimensional shape.

As previously mentioned, after the semi-rigid balloon has been inflated to perform the desired medical procedure, the balloon must be deflated (e.g., by the application of negative pressure to the balloon) so as to reduce its profile to permit withdrawal of the balloon from the patient, particularly if the balloon has been introduced through and endoscope or other introducer. FIG. 8 illustrates a partial side view of the idealized geometry of the individual cylindrical and conical balloon elements 64, 66, as shown in FIG. 7, that have been flattened into a 2-dimensional state. Due to energy considerations, this is the most prevalent folding configuration for an unconstrained balloon 62. By comparing FIGS. 7 and 8, it can be observed that when the cylindrical and conical balloon elements 64, 66 are converted from an inflated 3-dimensional state to a flattened 2-dimensional state, the projected shape of the cylindrical element 64 remains a rectangle while that of the conical element 66 changes from a triangle to a pie-shaped circular sector.

Figure 9:
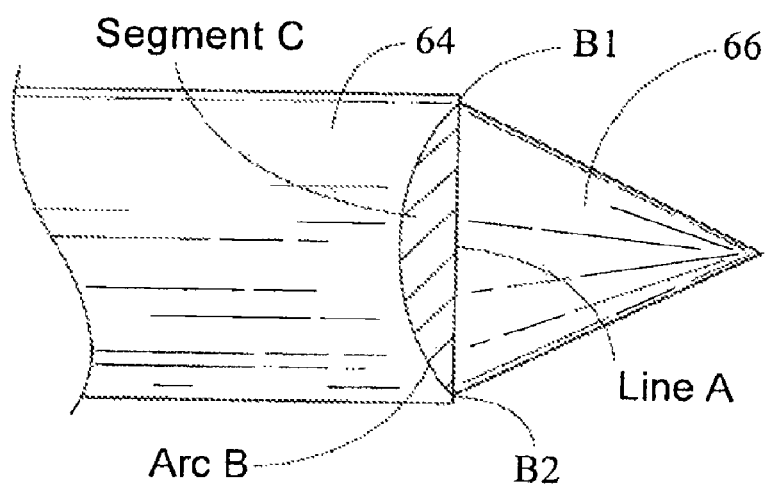
FIG. 9 illustrates the flattened balloon elements of FIG. 8 in an overlapping arrangement.

As shown in FIG. 8, a geometric incongruence exists between Line A of the flattened cylindrical element 64, and Arc B of the flattened conical element 66. This is because in the assembled balloon 62, all points along Arc B must remain affixed to Line A, including the most distant points B1 and B2. In FIG. 9, the projected shapes 64, 66 have been merged so that points B1 and B2 are disposed on Line A. The result is an area of geometric interference in the shape of circular Segment C (shown with cross-hatching). When an unconstrained balloon 62 is allowed to freely collapse upon the application of a negative deflation pressure, and assuming an approximation of 2-dimensional folding, the result is non-ideal crumpling of the balloon in the area of geometric interference (Segment C). And while the flattened balloon 62 may be efficiently rolled and packed into a relatively low-profile configuration for introduction through an endoscope and into the patient, the crumpled area remains highly inefficient in terms of material packing and thus tends to spoil the overall profile of the deflated balloon catheter 60.

While 2-dimensional folding is prevalent in an unconstrained balloon 62, many other folding configurations are possible, as illustrated in FIGS. 10-13. FIG. 10 illustrates the conical balloon element 66 in the flattened 2-dimensional configuration discussed thus far. This is also commonly referred to as a "2-wing" configuration, wherein the ends of the arc represent the tips of two wings. FIGS. 11-13 illustrate the geometry of 3-wing, 4-wing and 5-wing folding configurations, respectively, for conical balloon element 66. In general, the higher-wing configurations are more favorable over the lower-wing configurations because the magnitude of the geometric incongruence is reduced. This is because the geometric interference of the 2-wing configuration (Segment C of FIG. 9) is divided into several smaller segments. This is further illustrated in FIGS. 14-15.

Figure 14:
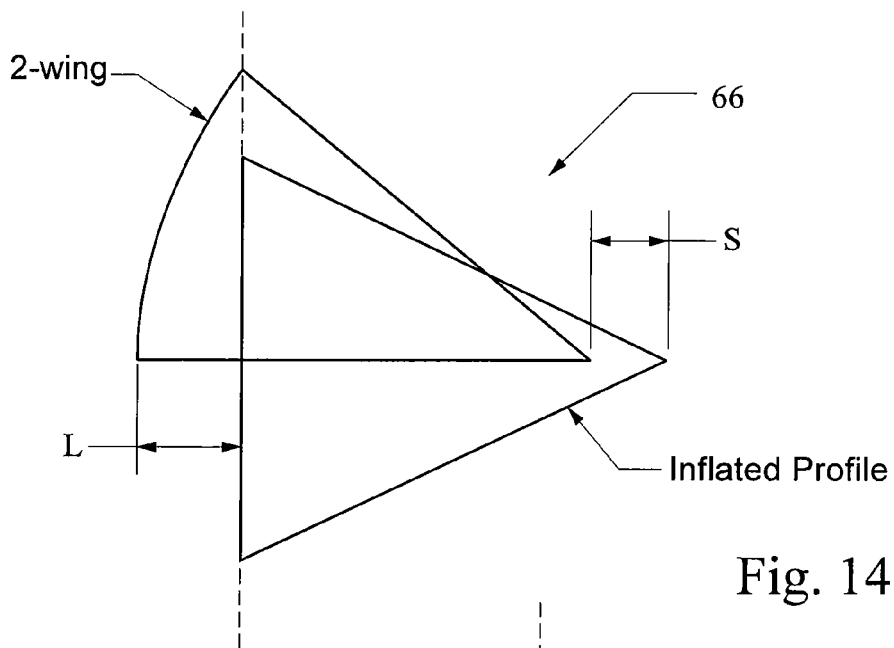
FIG. 14 is a geometric diagram illustrating the outline of one wing of a conical balloon element folded into a 2-wing configuration superimposed upon the projected profile of the same conical balloon element in its inflated 3-dimensional configuration.

FIG. 14 illustrates the upper wing of the conical balloon element 66 in the deflated (flattened) 2-wing configuration overlaid upon the triangular projection of the conical balloon element 66 in the 3-dimensional inflated configuration. The two projected shapes are axially aligned and positioned along the axis as if each were joined to the end of the same cylindrical balloon element 64 (see FIG. 9), which is represented by the dashed line. The parameter L is the length (measured along the longitudinal axis of the balloon) associated with the circular section of the geometric interference, and provides a quantitative measure of that phenomenon (and thus, the magnitude of interference crumpling). The parameter S illustrates a second phenomenon associated with the transition of the conical balloon element 66 from the inflated 3-dimensional profile to the deflated (and flattened) profile of a folded configuration, i.e., balloon shortening. In other words, because the ends of the arc(s) in any folded configuration lie upon the perimeter of the cone, which is coincident with the perimeter of the cylinder, the overall length of the balloon 62 must shorten at each end thereof by length S upon deflation of the balloon 62.

Figure 15:
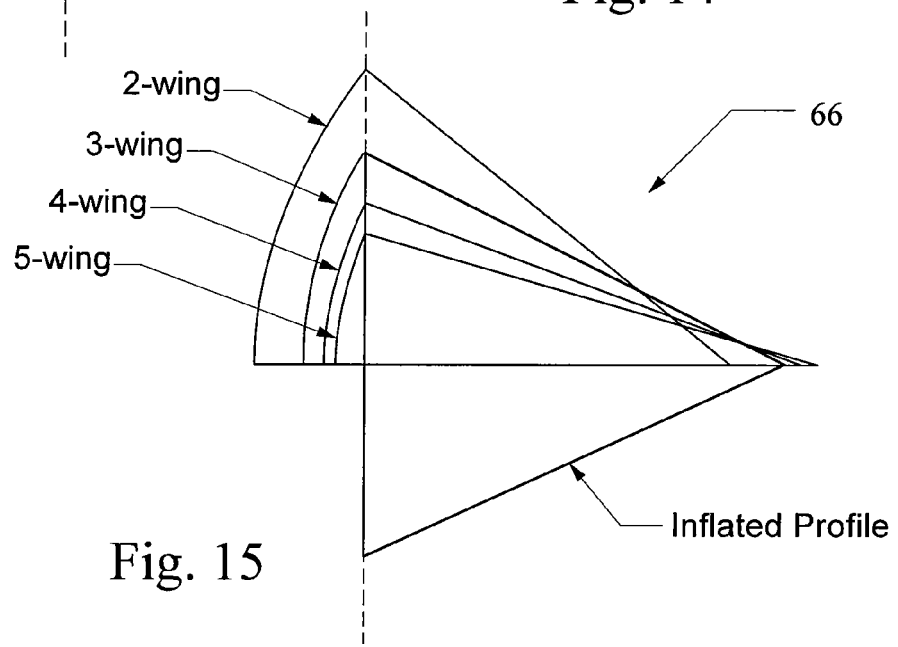
FIG. 15 is a geometric diagram illustrating the outline of one wing of a conical balloon element folded into a 2-wing, 3-wing, 4-wing and 5-wing configuration, each of which are superimposed upon the projected profile of the same conical balloon element in its inflated 3-dimensional configuration.

FIG. 15 likewise illustrates the upper wing of the conical balloon element 66 in the deflated (flattened) 2-wing configuration overlaid upon the triangular projection of the conical balloon element 66 in the 3-dimensional inflated configuration. In addition, FIG. 15 illustrates the projection of a single wing of the conical balloon element 66 in each of a 3-wing, 4-wing, and 5-wing folding configuration. And although the parameters L and S are not labeled, one can readily observe from the diagram the folding configuration significantly influences these two parameters. For example, the parameter L is dramatically reduced with each successive increase in the number of folded wings, demonstrating how higher wing-number configurations would incur less crumpling in the area of geometric interference. With respect to the parameter S, the effect of wing number is even more dramatic in that the parameter changes from positive with a 2-wing configuration, to negative with 4-wing and 5-wing configurations. In other words, the 4-wing and 5-wing configurations actually lengthen the balloon 62 (as opposed to shortening the balloon 62). Of significance, the 3-wing configuration has a parameter S that is nearly zero, indicating that the 3-wing configuration does not significantly alter the length of the balloon 62.

Figure 16:
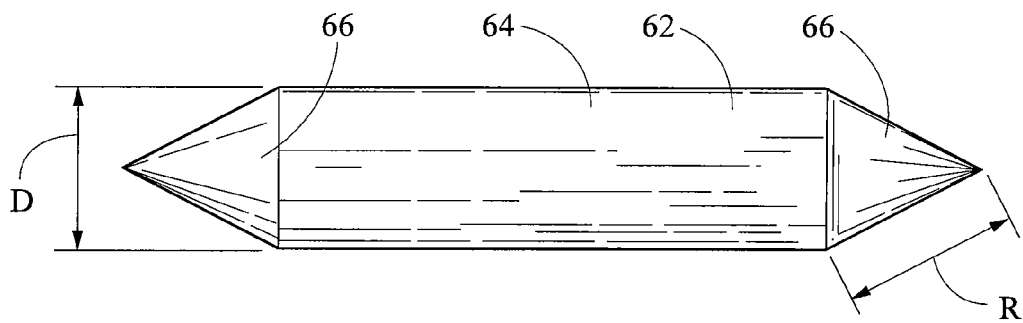
FIG. 16 is a geometric diagram illustrating the projected profile of an idealized balloon in its inflated 3-dimensional configuration.

The parameters L and S may be calculated for any such idealized balloon as long as other geometric parameters of the balloon are known. FIG. 16 illustrates one method of defining additional geometric balloon parameters that are sufficient to permit calculation of L and S for a given folding configuration. Specifically, those parameters are the diameter D of the cylindrical balloon element 64, and the cone radius R of the conical balloon element 66. Naturally, for any given balloon diameter, various "short" or "long" cones may be affixed. Thus it is useful to normalize by the balloon diameter D, and then reference an aspect ratio for the balloon in terms of R/D. Balloons of low aspect ratio will appear to short, stubby cones, while higher aspect ratio balloons will appear to have relatively longer cones. In all of the figures discussed thus far, the aspect ratio of the balloon 62 has been about 1.2. The parameters L and S may be similarly normalized, allowing their behavior to be plotted against the aspect ratio for various folding configurations. Those charts are presented in FIGS. 17 and 18, respectively.

Figure 17:
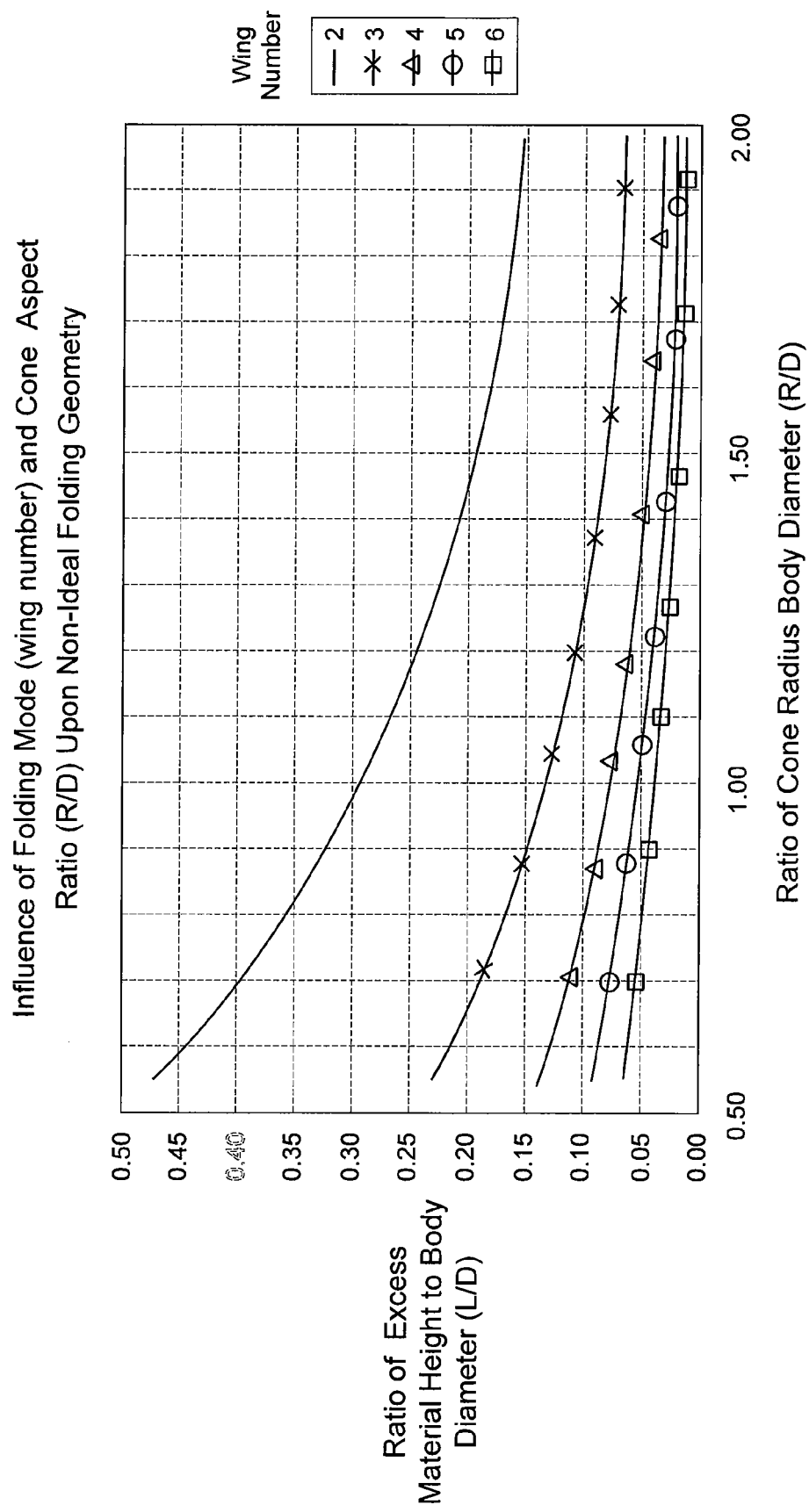
FIG. 17 is a chart illustrating the relationship of folding mode and cone aspect relation upon non-ideal folding geometry.

As illustrated in FIG. 17, it can be observed that L generally drops gradually and approaches an asymptotic value as the aspect ratio increases. From a study of the mathematical function describing L, which is a trigonometric function, it can be deduced that the asymptotic value being approached is zero, regardless of wing number. For the range of aspect ratios shown, L is reduced by approximately ½ in going from a 2-wing to a 3-wing folding configuration. Further reductions, on the order of an additional ⅓ each, are gained in going from a 3-wing to a 4-wing configuration, and in going from a 4-wing to a 5-wing configuration. In the move from a 5-wing to a 6-wing configuration, the reduction in L is approximately ¼, so that a trend of diminished returns seems to be evident.

Figure 18:
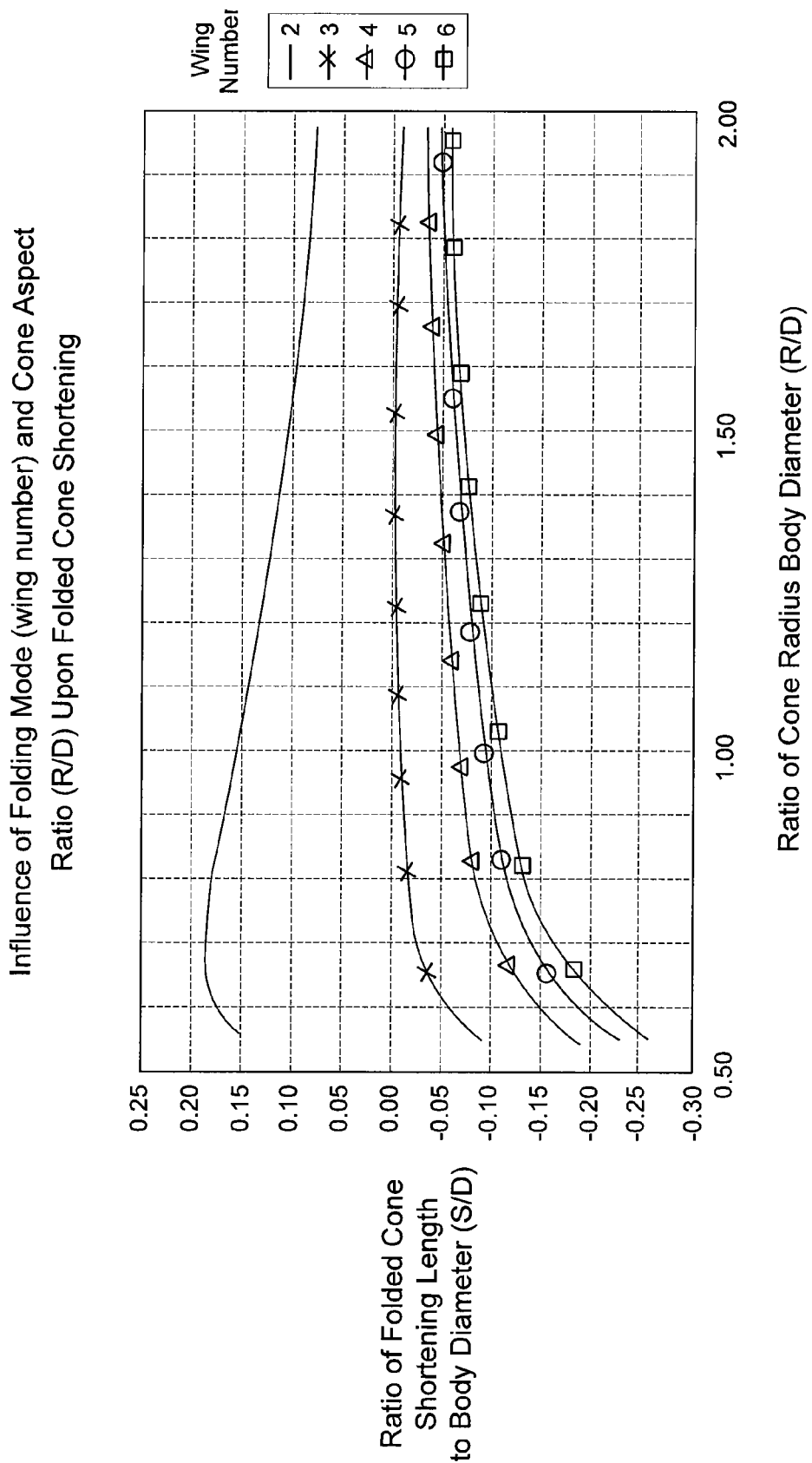
FIG. 18 is a chart illustrating the relationship of folding mode and cone aspect relation upon folded cone shortening.

In FIG. 18, it can be observed that S also approaches an asymptotic value as the aspect ratio increases. And again, from the mathematical function describing S, which is also a trigonometric function, it can be deduced that S approaches zero in all cases. It should be noted that, for the range of aspect ratios shown, the behavior of S for 2-wing and 3-wing configurations are different from one another and from the behaviors for wing numbers of 4 and above, which all behave similarly to one another. For the 2-wing folding configuration, S is entirely positive, first rising before dropping asymptotically towards zero. For the 3-wing configuration, S starts out negative, rises to cross zero at an R/D equal to about one, then peaks and gradually approaches zero from the positive side. For 4 and higher wing configurations, S is entirely negative and approaches zero asymptotically in a seemingly first order fashion.

The present invention is directed to control mechanisms for improving the profile of slip-joint balloon catheters upon deflation, and in particular, for reducing L (i.e., crumpling) via control of S (i.e., balloon shortening or lengthening). In other words, if balloon shortening during deflation can be prevented, or if a prescribed amount of balloon lengthening can be induced, folding into the higher-wing configurations can be achieved. In turn, this forces a reduction in L, which reduces crumpling and improves the profile of the balloon for ease of insertion into and withdrawal from the patient. In short, the control mechanisms of the present invention are configured to promote the refolding of a slip joint balloon into at least a 3-wing configuration by controlling the length of the balloon during deflation. Several embodiments of balloon folding control mechanisms according to the present invention will now be described in connection with FIGS. 19-25.

Figure 19:
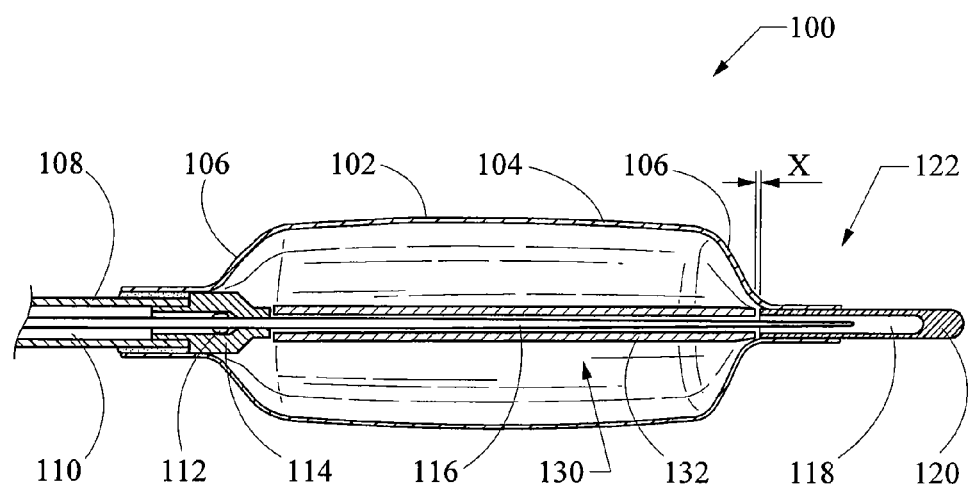
FIG. 19 is a cross-sectional side view of the distal portion of a slip joint balloon catheter comprising a first embodiment of a balloon folding control mechanism in accordance with the present invention.

A first embodiment of a balloon catheter 100 of the present invention is depicted in FIG. 19, which illustrates the distal portion (i.e., the balloon portion) of the balloon catheter 100. The balloon catheter 100 includes a balloon 102 having a cylindrical central element 104 and a pair of conical end elements 106. The balloon 102 is typically manufactured from a non-elastomeric material (e.g., a semi-rigid or non-compliant material), and preferably comprises a translucent, transparent or optically clear film. For example, the balloon 102 could be manufactured from a biocompatible polymer such as polyamide, polyurethane, polyester, polyolefin, polyethylene terephthalate and the like. The balloon 102 is generally manufactured as a unitary structure and in the shape of its 3-dimensional inflated stated.

The proximal end of the balloon 102 is fixedly connected to the distal end of a flexible elongate outer catheter 108. The proximal end of the outer catheter 108 includes a hub (not shown) that is configured to attach to an inflation device such a standard medical syringe. An inflation lumen 110 extends through the outer catheter 108 and is in fluid communication with the hub. The distal end of the inflation lumen 110 is in fluid communication with the interior of the balloon 102 via one or more apertures 112 disposed through the side of a metal insert 114. The metal insert 114 is press fit into the distal end of the outer catheter 108, and is configured to prevent the balloon 102 from occluding (blocking) the apertures 112 during deflation. Thus, an inflation fluid may be injected into, or withdrawn from, the interior of the balloon 102 by an inflation device attached to the hub via inflation lumen 110 and apertures 112.

The balloon catheter 100 further comprises an elongate stiffening member 116 disposed within the lumen 110 of the outer catheter 108. The diameter or cross-sectional area of the stiffening member 116 is generally less than the diameter or cross-sectional area of the lumen 110 so as to allow the passage of the inflation fluid between the hub (i.e., the inflation device) and the interior of the balloon 102. In other words, the diameter of the stiffening member 116 is less than that of the lumen 110 so as to create a cavity between the outside surface of the stiffening member 116 and the inside surface of the lumen 110 sufficient for the passage of the inflation lumen. Alternatively, the outer catheter 108 may comprise one or more separate lumens for the passage of the inflation fluid, and the stiffening member 116 may be disposed with a non-inflation lumen. The catheter 108 may also comprise additional lumens configured for other functions, such as for the injection of contrast or medications, or for the passage of a wire guide. The design of multi-lumen catheters is well known to those skilled in the art.

The stiffening member 116 is connected at or near its proximal end to the hub (not shown). The distal end of the stiffening member 116 extends distally from the distal end of the outer catheter 108 (i.e., through insert 114), through the interior of the balloon 102, and into a sleeve 118 formed in the distal end of the balloon 102. In the embodiment shown, the sleeve 118 is formed by an end cap 120 fixed to the distal end of the balloon 102. The end cap 120 provides an air tight seal with the balloon 102 and is rounded at its distal end to facilitate ingress of the balloon catheter 100 into and through the patient's bodily lumen and prevent the end cap 120 from puncturing or injuring the walls of the bodily lumen. The end cap 120 may be manufactured from a pliable plastic material to further promote the ingress of the balloon catheter 100 and reduce irritation that may be caused thereby.

The stiffening member 116 preferably comprises a nitinol wire having a tapered distal end. A coil spring (not shown) may be affixed about the distal end of the stiffening member 116 to provide for a transition in flexibility between the stiffening member 116 and the end cap 120. The distal end of the stiffening member 116 slidably engages with sleeve 118 to form a slip joint connection 122. The slip joint 122 allows the distal end of the balloon 102 to axially move or translate with respect to the distal end of stiffening member 116. This configuration allows the overall axial or longitudinal length of balloon 102 to change during inflation or deflation without transferring tensile or compressive forces to either outer catheter 108 or the stiffening member 116. The advantages provided by the slip joint 122 are more fully disclosed and explained in US 2003/0236495 and US 2004/0236366, both entitled "Non-Buckling Balloon Catheter", the entire contents of which are incorporated herein by reference. The advantages of slip-jointed balloon catheters are further disclosed and explained in U.S. Provisional Application No. 60/922,769, filed Apr. 10, 2007, and entitled "Non-Buckling Balloon Catheter With Spring Loaded Floating Flexible Tip", the entire contents of which is also incorporated herein by reference.

Nevertheless, and for the reasons explained above, further advantages may be imparted to a slip-jointed balloon catheter by implementing positive control over the length of the balloon during deflation. In particular, the balloon catheter 100 of the of the present invention comprises a balloon folding control mechanism 130 for controlling the length of the balloon 102 during deflation so as to promote the refolding of the balloon 102 into at least a 3-wing configuration. In the particular embodiment depicted in FIG. 19, control mechanism 130 comprises a tubular member 132 disposed about the portion of the stiffening member 116 extending through the interior of the balloon 102. The tubular member 132 is configured to act as back stop or spacer to prevent the distal end of the balloon 102 from moving too far proximally during deflation, i.e., from shortening excessively. As explained above, if the length of the balloon 102 is not constrained, the balloon will tend to shorten by an amount necessary to achieve a 2-wing folding configuration, which due to energy considerations is the most prevalent folding configuration. This will lead to excessive crumpling of the balloon 102. Moreover, the 2-wing folding configuration tends to result in an oversized deflated cross-section. The tubular member 132, on the other hand, prevents the balloon 102 from shortening excessively during inflation, thereby promoting a higher number folding configuration and reducing crumpling of the balloon 102.

In the particular embodiment illustrated, the tubular member 132 has a length that is shorter than the spacing between the distal face of the insert 114 and the proximal face of the end cap 120 by a distance X when the balloon 102 is in the inflated state. Thus, distance X represents the maximum amount of shortening that the balloon 102 will be allowed to undergo during deflation, and is selected based upon the aspect ratio of the balloon and the folding mode desired. For example, with respect to the balloon catheter 100 illustrated in FIG. 19, the balloon 102 has an aspect ratio of about 1.8. With reference to FIG. 18, and assuming that a 3-wing folding configuration is desired, a slight amount of shortening is required such that the ratio S/D would be about 0.0005. Thus, in order to facilitate and/or promote the desired 3-wing folding configuration, the length of the tubular member 132 should be selected to provide a spacing of about 0.005 D.

The diameter of the tubular member 132 may also assist in promoting higher wing-number folding configurations. In particular, it has been speculated that the relatively large diameter of the tubular member 132 (as compared to that of the stiffening member 116) tends to prevent the balloon 102 from folding into a 2-wing configuration. However, the mechanism by which this occurs, if at all, is not known at this time.

The tubular member 132 may also provide other advantages in addition to promoting a higher-wing folding configuration and/or inhibiting balloon crumpling during deflation. In particular, tubular member 132 may provide a means for evacuating fluid from the distal end of the balloon 102 if the proximal portion of the balloon 102 collapses and seals about the stiffening member 116 during deflation. This may be accomplished by configuring the tubular member 132 to provide a pathway for the passage of inflation fluid from the distal end of the balloon 102 to the apertures 112 at the proximal end of the balloon 102. In one embodiment, the tubular member 132 may comprise a series of openings (not shown) disposed therealong through which the inflation fluid may pass into and along the interior of the tubular member 132.

Figure 20:
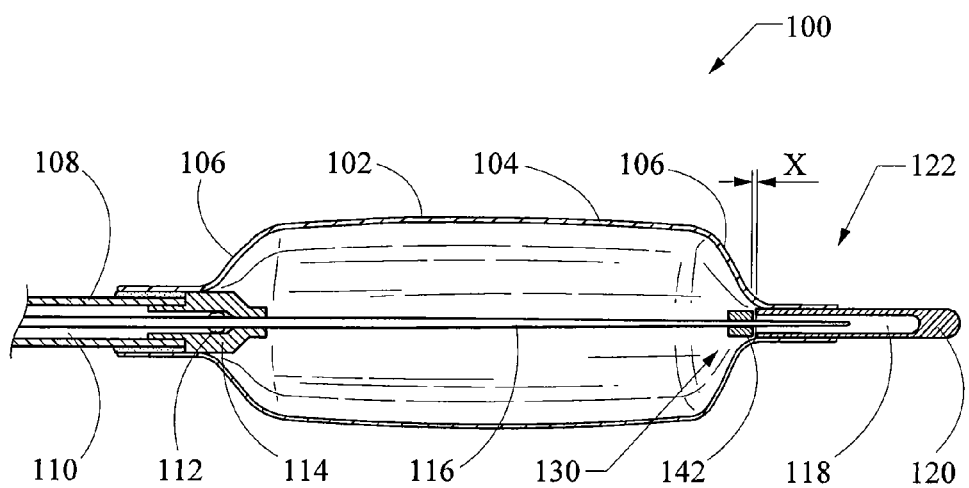
FIG. 20 is a cross-sectional side view of the distal portion of a slip joint balloon catheter comprising a second embodiment of a balloon folding control mechanism in accordance with the present invention.

FIG. 20 is a cross-sectional side view of the distal portion of the slip joint balloon catheter 100 of FIG. 19. However, this figure illustrates a second embodiment of a balloon folding control mechanism 130 in accordance with the present invention. In this particular embodiment, the balloon folding control mechanism 130 comprises a stop collar 142 affixed to the stiffening member 116 at a specific distance X from the proximal face of the end cap 120. As explained above in connection with FIG. 19, the distance X represents the maximum amount of shortening that the balloon 102 will be allowed to undergo during deflation, and is selected based upon the aspect ratio of the balloon and the folding mode desired. For example, with respect to the balloon catheter 100 illustrated in FIGS. 19 and 20, the balloon 102 has an aspect ratio of about 1.8. With reference to FIG. 18, and assuming that a 3-wing folding configuration is desired, a slight amount of shortening is required such that the ratio S/D would be about 0.0005. Thus, in order to facilitate and/or promote the desired 3-wing folding configuration, the stop collar 142 should be affixed to the stiffening member 116 so as provide a spacing X of about 0.005 D.

Figure 21:
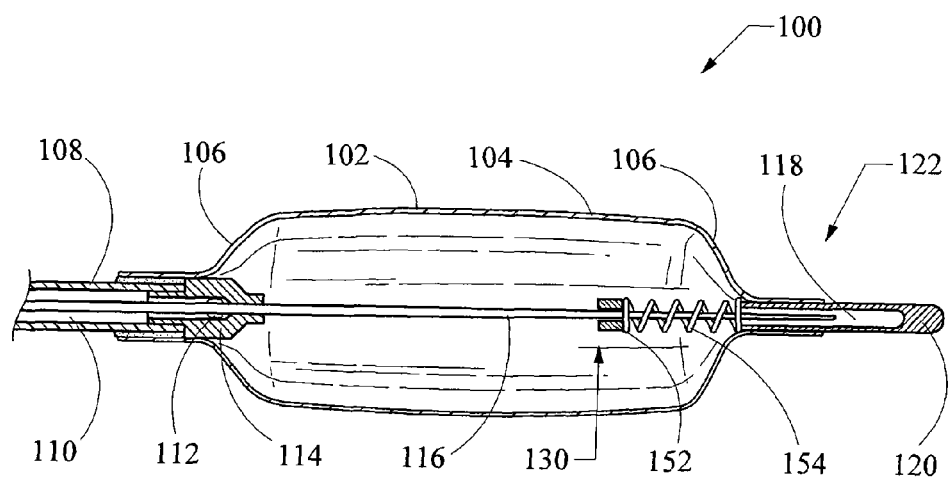
FIG. 21 is a cross-sectional side view of the distal portion of a slip joint balloon catheter comprising a third embodiment of a balloon folding control mechanism in accordance with the present invention.

FIG. 21 is a cross-sectional side view of the distal portion of the slip joint balloon catheter 100 of FIG. 19. However, this figure illustrates a third embodiment of a balloon folding control mechanism 130 in accordance with the present invention. In this particular embodiment, the balloon folding control mechanism 130 comprises a stop collar 152 in combination with a compression spring 154. The stop collar 152 is affixed to the stiffening member 116 and engages the proximal end of the spring 154. The spring 154 is positioned between the stop collar 152 and the proximal face of the end cap 120, and is configured to apply a biasing force therebetween. The position of the stop collar 152 and/or the length of the spring 154 may be selected to ensure that the spring 154 engages the end cap 120, or engages the end cap 120 at a specified force level, thereby inhibiting excessive shortening of the balloon 102. Because the spring 154 may be pre-loaded in compression, it is capable of lengthening and thus may be designed to encourage lengthening of the balloon 102 during deflation by a specified amount. The amount of balloon lengthening may be selected according to the balloon 102 aspect ratio and desired folding configuration. This can be particularly advantageous in promoting folding into higher wing-number configurations. For example, and by reference to FIG. 18, it can be observed that for a balloon with an aspect ratio of about 1.1, a 4-wing folding configuration requires lengthening such that S/D would be slightly greater than 0.05. Thus, if a compression spring 154 were to be employed with enough biasing force to encourage displacement of the distal end of the balloon 102 (relative to its proximal end) by an amount equal o about 0.05 D, a 4-wing folding configuration would be achieved during deflation.

Figure 22:
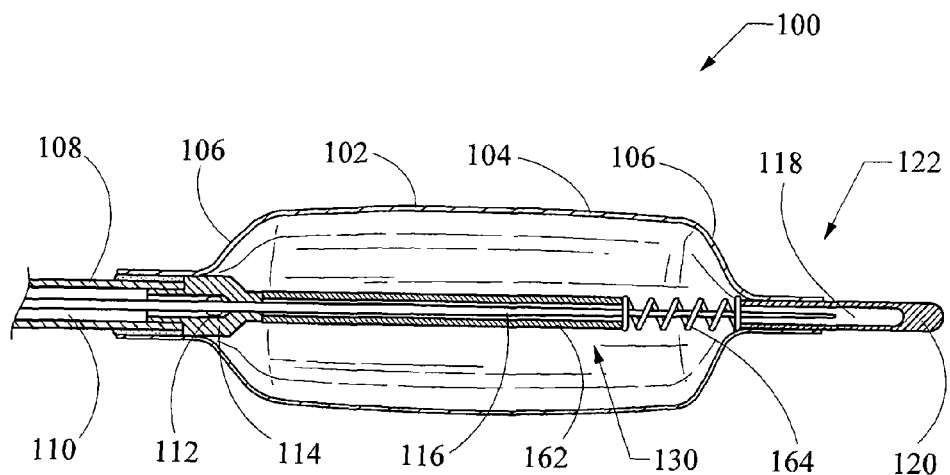
FIG. 22 is a cross-sectional side view of the distal portion of a slip joint balloon catheter comprising a fourth embodiment of a balloon folding control mechanism in accordance with the present invention.

FIG. 22 is a cross-sectional side view of the distal portion of the slip joint balloon catheter 100 of FIG. 19. However, this figure illustrates a fourth embodiment of a balloon folding control mechanism 130 in accordance with the present invention. In this particular embodiment, the balloon folding control mechanism 130 comprises a tubular member 162 in combination with a compression spring 164. The tubular member 162 acts as a spacer between the distal face of the insert 114 and the proximal end of the spring 164. Thus, the tubular member 162 transfers the force from the spring 164 to the insert 114. The spring 164 is essentially the same in configuration and function as the spring 154 of the embodiment illustrated in FIG. 21.

Figure 23:
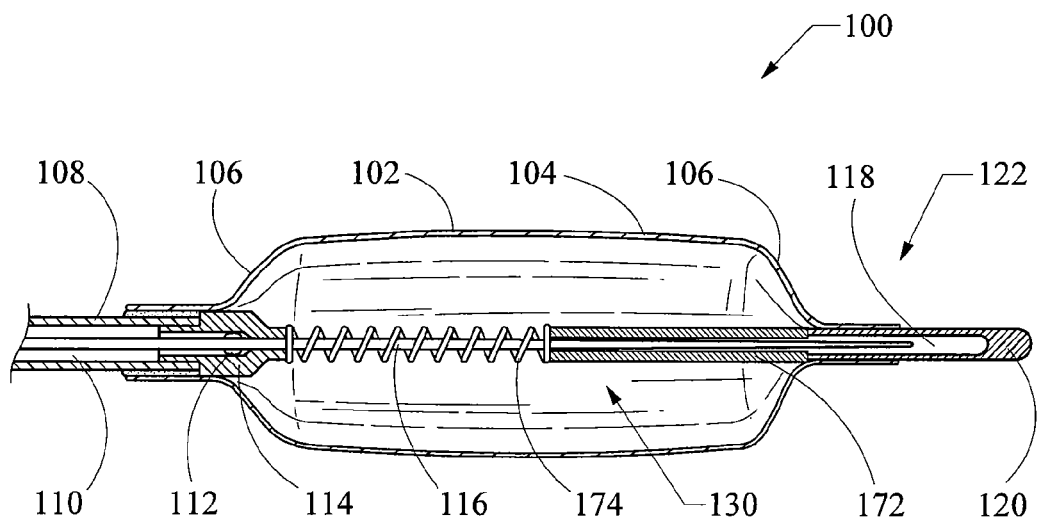
FIG. 23 is a cross-sectional side view of the distal portion of a slip joint balloon catheter comprising a fifth embodiment of a balloon folding control mechanism in accordance with the present invention.

FIG. 23 is a cross-sectional side view of the distal portion of the slip joint balloon catheter 100 of FIG. 19. However, this figure illustrates a fifth embodiment of a balloon folding control mechanism 130 in accordance with the present invention. In this particular embodiment, the balloon folding control mechanism 130 comprises a tubular member 172 and a compression spring 174, and is therefore similar to the arrangement of FIG. 22. However, the positions of the tubular member 172 and the compression spring 174 are reversed as compared to the arrangement of FIG. 22. Nevertheless, the function of these components is essentially the same.

Figure 24:
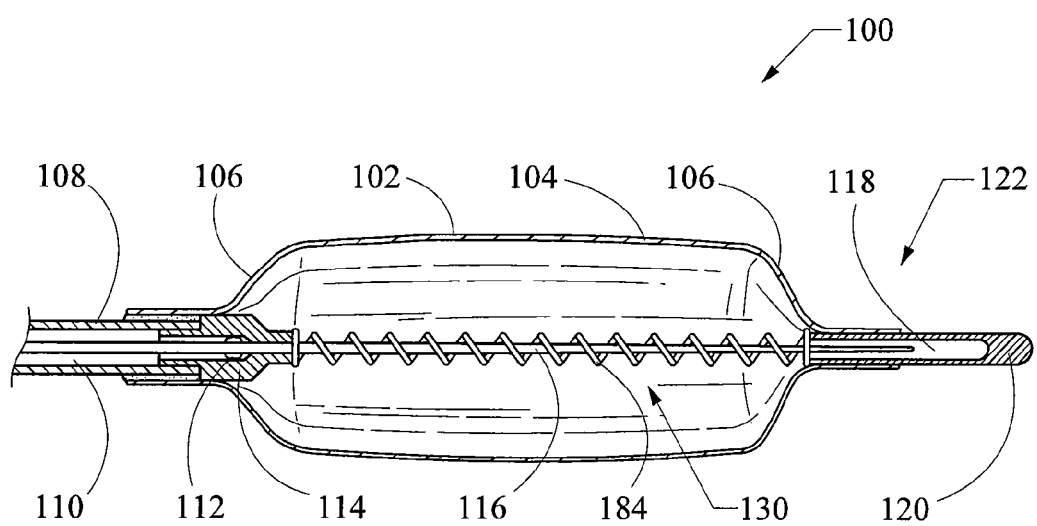
FIG. 24 is a cross-sectional side view of the distal portion of a slip joint balloon catheter comprising a sixth embodiment of a balloon folding control mechanism in accordance with the present invention.

FIG. 24 is a cross-sectional side view of the distal portion of the slip joint balloon catheter 100 of FIG. 19. However, this figure illustrates a sixth embodiment of a balloon folding control mechanism 130 in accordance with the present invention. In this particular embodiment, the balloon folding control mechanism 130 comprises a compression spring 184 only. The compression spring 184 has a length that traverses the interior of the balloon 102 and engages both the distal face of the insert 114 and the proximal face of the end cap 120. In any event, the function of the spring 184 is essentially the same as in the previously described embodiments.

Figure 25:
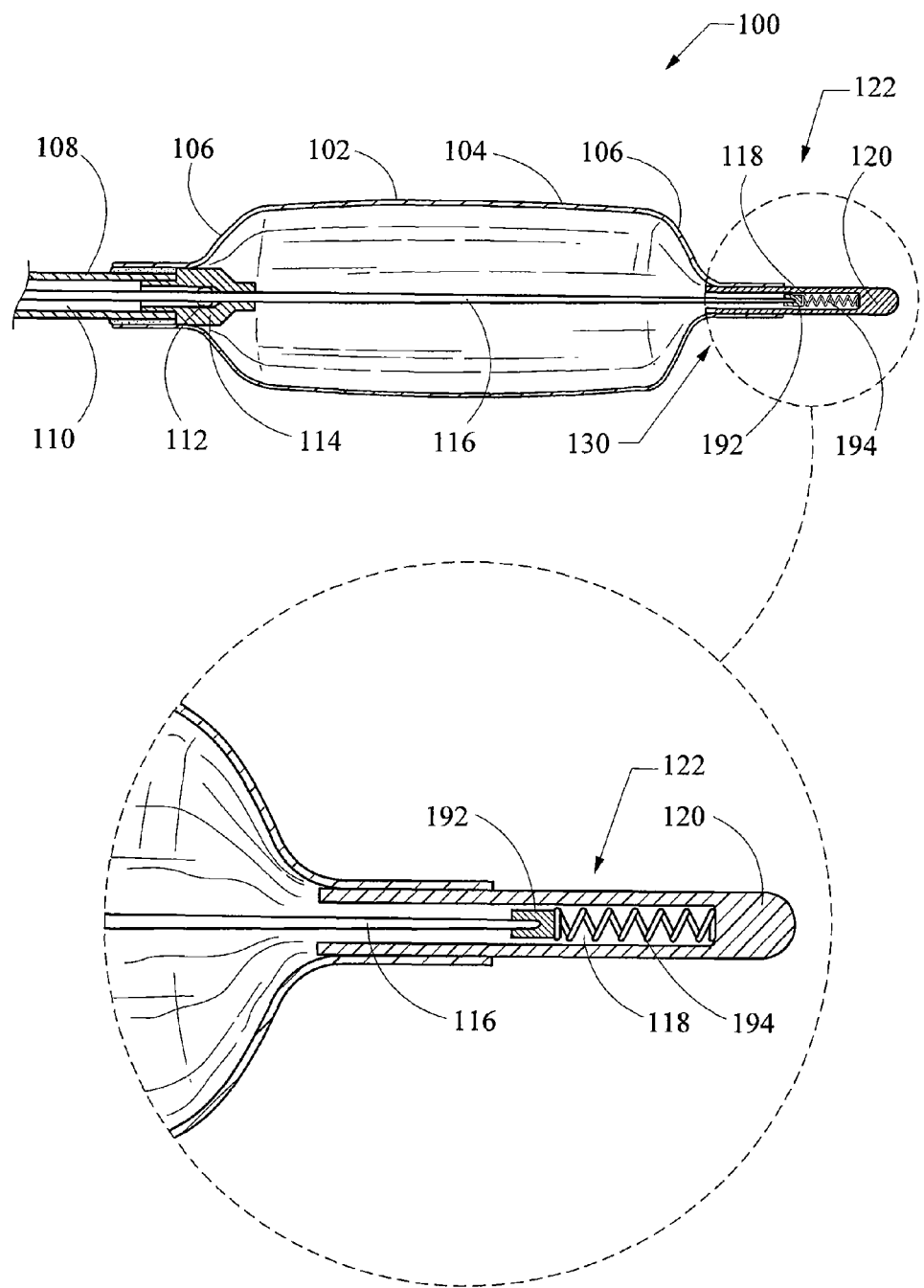
FIG. 25 is a cross-sectional side view of the distal portion of a slip joint balloon catheter comprising a seventh embodiment of a balloon folding control mechanism in accordance with the present invention.

FIG. 25 is a cross-sectional side view of the distal portion of the slip joint balloon catheter 100 of FIG. 19. However, this figure illustrates a seventh embodiment of a balloon folding control mechanism 130 in accordance with the present invention. In this particular embodiment, the balloon folding control mechanism 130 comprises a stop collar 192 and a spring 194. The stop collar 192 is affixed to the distal end of the stiffening member 116 and is disposed within the sleeve 118 of the end cap 120. The spring 194 is likewise disposed within the sleeve 118 of the end cap 120, and engages the distal face of the stop collar 192 and the distal end of the sleeve 118. In any event, the function of the spring 184 is essentially the same as in the previously described embodiments.

Any other undisclosed or incidental details of the construction or composition of the various elements of the disclosed embodiments of the present invention are not considered to be critical to the achievement of the advantages of the present invention, so long as the elements possess the attributes required to perform as disclosed herein. The selection of these and other details of construction are believed to be well within the ability of one of ordinary skill in the relevant art in view of the present disclosure. Illustrative embodiments of the present invention have been described in considerable detail for the purpose of disclosing practical, operative structures whereby the invention may be practiced advantageously. The designs described herein are intended to be exemplary only. The novel characteristics of the invention may be incorporated in other structural forms without departing from the spirit and scope of the invention.

What is claimed is:

1. A balloon catheter comprising:
   an inflatable balloon comprising a balloon wall defining an interior volume, the balloon further comprising a distal end, a proximal end, and a central portion disposed therebetween;
   a catheter comprising an elongated shaft extending along a longitudinal axis between a distal end portion and a proximal end portion, the proximal end portion comprising a connector configured to engage an inflation device, the distal end portion fixedly connected to the proximal end of the balloon, and a lumen extending through the shaft and in fluid communication with the interior volume of the balloon;
   an end cap fixedly connected to the distal end of the balloon;
   a stiffening member extending distally from the distal end portion of the catheter and through the interior volume of the balloon, the stiffening member being engaged with the end cap; and
   a balloon folding control mechanism configured to promote refolding of the balloon into a predetermined folding configuration upon deflation of the balloon,
   wherein the balloon folding control mechanism is configured to apply a distally directed biasing force to the distal end of the balloon relative to the proximal end of the balloon,
   wherein the balloon folding control mechanism comprises a compression spring that is operably engaged with the distal end of the balloon at least when the balloon is in a deflated state, and
   wherein the compression spring is disposed about the stiffening member and is operably engaged between the distal end of the balloon and a stop collar affixed to the stiffening member so as to apply a biasing force therebetween.

2. The balloon catheter according to claim 1 wherein the end cap comprises a sleeve extending partially therethrough, the sleeve being defined by an interior volume of the end cap, and further wherein the stiffening member is slidably engaged with the sleeve of the end cap so as to permit longitudinal movement of the distal end of the balloon relative to the proximal end of the balloon.

3. The balloon catheter according to claim 2 wherein the end cap comprises a polyurethane tube fixedly connected to the distal end of the balloon.

4. The balloon catheter according to claim 2 wherein the sleeve comprises a distal terminus that is spaced away from a distal end of the stiffening member so as to permit axial movement of the distal end of the stiffening member relative to the distal terminus of the sleeve.

5. The balloon catheter according to claim 1 wherein the stop collar is spaced away from the distal end of the balloon when the balloon is in an inflated state.

6. The balloon catheter according to claim 2 wherein the balloon folding control mechanism is disposed within the sleeve of the end cap.

7. The balloon catheter according to claim 1 wherein the compression spring is disengaged from the distal end of the balloon when the balloon is in an inflated state.

8. The balloon catheter according to claim 1 wherein the distally directed biasing force applied by the compression spring to the distal end of the balloon is sufficient to lengthen the balloon upon deflation of the balloon.

9. The balloon catheter according to claim 1 wherein the balloon folding control mechanism is configured to limit proximal movement of the distal end of the balloon relative to the proximal end of the balloon upon deflation of the balloon.

10. The balloon catheter according to claim 1 wherein the balloon folding control mechanism is configured to promote a balloon folding configuration of 3-wings or higher upon deflation of the balloon.

11. The balloon catheter according to claim 1 wherein the balloon wall comprises one of a non-elastic material, a non-compliant material, and a semi-rigid material.

12. The balloon catheter according to claim 1 wherein the stiffening member comprises an elongate proximal portion extending longitudinally through the lumen of the shaft of the catheter.

13. The balloon catheter according to claim 12 wherein the stiffening member comprises an elongate nitinol wire.

14. The balloon catheter according to claim 12 wherein the stiffening member comprises a tapered distal end portion.

15. The balloon catheter according to claim 1 further comprising an inflation device for inflating or deflating said balloon, said inflation device being attached to the connector on the proximal end portion of the catheter.

16. A balloon catheter comprising:
    an inflatable balloon comprising a balloon wall defining an interior volume, the balloon further comprising a distal end, a proximal end, and a central portion disposed therebetween;
    a catheter comprising an elongated shaft extending along a longitudinal axis between a distal end portion and a proximal end portion, the proximal end portion comprising a connector configured to engage an inflation device, the distal end portion fixedly connected to the proximal end of the balloon, and a lumen extending through the shaft and in fluid communication with the interior volume of the balloon;
    an end cap fixedly connected to the distal end of the balloon;
    a stiffening member extending distally from the distal end portion of the catheter and through the interior volume of the balloon, the stiffening member being engaged with the end cap; and
    a balloon folding control mechanism configured to promote refolding of the balloon into a predetermined folding configuration upon deflation of the balloon,
    wherein the balloon folding control mechanism is configured to apply a distally directed biasing force to the distal end of the balloon relative to the proximal end of the balloon,
    wherein the balloon folding control mechanism comprises a compression spring that is operably engaged with the distal end of the balloon at least when the balloon is in a deflated state, and wherein the compression spring is disposed about the stiffening member and is operably engaged with a tubular member, wherein the compression spring and the tubular member are operably engaged between the distal and proximal ends of the balloon so as to apply a biasing force therebetween.

17. The balloon catheter according to claim 16 wherein the end cap comprises a sleeve extending partially therethrough, the sleeve being defined by an interior volume of the end cap, and further wherein the stiffening member is slidably engaged with the sleeve of the end cap so as to permit longitudinal movement of the distal end of the balloon relative to the proximal end of the balloon.

18. The balloon catheter according to claim 17 wherein the end cap comprises a polyurethane tube fixedly connected to the distal end of the balloon.

19. The balloon catheter according to claim 17 wherein the sleeve comprises a distal terminus that is spaced away from a distal end of the stiffening member so as to permit axial movement of the distal end of the stiffening member relative to the distal terminus of the sleeve.

20. The balloon catheter according to claim 17 wherein the balloon folding control mechanism is disposed within the sleeve of the end cap.

21. The balloon catheter according to claim 16 wherein the compression spring is disengaged from the distal end of the balloon when the balloon is in an inflated state.

22. The balloon catheter according to claim 16 wherein the distally directed biasing force applied by the compression spring to the distal end of the balloon is sufficient to lengthen the balloon upon deflation of the balloon.

23. The balloon catheter according to claim 16 wherein the balloon folding control mechanism is configured to limit proximal movement of the distal end of the balloon relative to the proximal end of the balloon upon deflation of the balloon.

24. The balloon catheter according to claim 16 wherein the balloon folding control mechanism is configured to promote a balloon folding configuration of 3-wings or higher upon deflation of the balloon.

25. The balloon catheter according to claim 16 wherein the balloon wall comprises one of a non-elastic material, a non-compliant material, and a semi-rigid material.

26. The balloon catheter according to claim 16 wherein the stiffening member comprises an elongate proximal portion extending longitudinally through the lumen of the shaft of the catheter.

27. The balloon catheter according to claim 26 wherein the stiffening member comprises an elongate nitinol wire.

28. The balloon catheter according to claim 26 wherein the stiffening member comprises a tapered distal end portion.

29. The balloon catheter according to claim 16 further comprising an inflation device for inflating or deflating said balloon, said inflation device being attached to the connector on the proximal end portion of the catheter.

\* \* \* \* \*